(12) United States Patent
Fan et al.

(10) Patent No.: US 10,647,970 B2
(45) Date of Patent: May 12, 2020

(54) L-TYPE AMYLASE VARIANT AND USE THEREOF

(71) Applicant: Nanjing Bestzyme Bio-Engineering Co., LTD., Nanjing (CN)

(72) Inventors: Yan Fan, Nanjing (CN); Yan Sun, Nanjing (CN); Hong Xu, Nanjing (CN)

(73) Assignee: Nanjing Bestzyme Bio-Engineering Co., LTD., Nanjing (CN)

( * ) Notice: Subject to any disclaimer, the term of this patent is extended or adjusted under 35 U.S.C. 154(b) by 29 days.

(21) Appl. No.: 15/989,534

(22) Filed: May 25, 2018

(65) Prior Publication Data
US 2018/0340161 A1 Nov. 29, 2018

(30) Foreign Application Priority Data
May 25, 2017 (CN) .......................... 2017 1 0377634

(51) Int. Cl.
C12N 9/26 (2006.01)
C12N 9/28 (2006.01)
C12N 15/56 (2006.01)
C12N 1/21 (2006.01)
C07K 19/00 (2006.01)

(52) U.S. Cl.
CPC .... C12N 9/2417 (2013.01); C12Y 302/01001 (2013.01); C07K 2319/00 (2013.01)

(58) Field of Classification Search
None
See application file for complete search history.

(56) References Cited

U.S. PATENT DOCUMENTS

| | | | | |
|---|---|---|---|---|
| 8,809,031 B2 * | 8/2014 | England | ............... | C12N 9/2417 435/202 |
| 2005/0049165 A1 * | 3/2005 | Kottwitz | ............ | C11D 3/38609 510/392 |
| 2015/0353871 A1 * | 12/2015 | Oebro | ................ | C11D 3/38636 510/393 |

OTHER PUBLICATIONS

Uniprot, Accession No. Q208A7, 2017, www.uniprot.org.*
Guo et al., Protein tolerance to random amino acid change, Proc. Natl. Acad. Sci. USA, 2004, 101, 9205-10.*
Hagihara et al., Improvement of thermostability of a calcium-free alpha-amylase from an alkaliphilic *Bacillus* sp. by protein engineering, J. Appl. Glycosci., 2002, 49, 281-89.*
Nonaka et al., Crystal Structure of Calcium-free alpha-Amylase from *Bacillus* sp. Strain KSM-K38 (AmyK38) and Its Sodium Ion Binding Sites, J. Biol. Chem., 2003, 278, 24818-24.*
Nonnatural, Meriam-Webster Thesaurus, www.merriam-webster.com/thesaurus/nonnatural retrieved Aug. 15, 2019.*
Hagihara et al., Deduced amino-acid sequence of a calcium-free a-amylase from a strain of Bacillus, Eur. J. Biochem., 2001, 268, 3974-3982.*
Machius et al., "Activation of *Bacillus licheniformis* α-amylase through a disorder→order transition of the substrate-binding site mediated by a calcium-sodium-calcium metal triad," *Structure* 6:281-292, 1998.

* cited by examiner

*Primary Examiner* — Robert B Mondesi
*Assistant Examiner* — Todd M Epstein
(74) *Attorney, Agent, or Firm* — Klarquist Sparkman, LLP

(57) ABSTRACT

The present invention discloses an L-type amylase variant and use thereof. The α-amylase variant is obtained by deleting the first N-terminal amino acid residue V from the α-amylase of *B. licheniformis* and replacing it with three other amino acid residues DGL. The α-amylase variant provided by the present invention has high catalytic activity under the acidic conditions of pH 5.0-5.8 and a high temperature of 100° C. or above. The acid resistance and thermal stability of these α-amylase variants are suitable for starch liquefaction.

9 Claims, 5 Drawing Sheets

Specification includes a Sequence Listing.

L-TYPE AMYLASE VARIANT AND USE THEREOF

CROSS-REFERENCE TO RELATED APPLICATION

This application claims the benefit under 35 U.S.C. § 119 of the earlier filing date of Chinese application No. CN 201710377634.2, filed on May 25, 2017, herein incorporated by reference in its entirety.

FIELD OF THE INVENTION

The present invention relates to the field of enzyme engineering, and in particular to an L-type amylase variant and use thereof.

BACKGROUND OF THE INVENTION

In the industry, the hydrolysis of starch starts mainly with α-amylase. The synergistic application of these α-amylases derived from microorganisms and other enzyme species, such as pullulanase, glucoamylase and glucose isomerase, can effectively break down starch macromolecules, and the produced small-molecule polysaccharides or monosaccharides have many applications in food manufacturing, grain processing, beer processing, and alcohol production. The α-amylase belongs to one kind of saccharifying hydrolase, with a main structural feature of (α/β) 8 folding, which contains a special starch substrate binding site with a length of generally no more than 10 saccharide monomers. However, the binding sites of several amylases can work together to perform multi-site binding to successfully cleave starch macromolecules.

The α-amylase can effectively cleave α-1,4 glycosidic bond in the starch substrate, thereby rapidly reducing molecular weight and viscosity of the starch substrate, with the products being mainly dextrins of different lengths. There are different kinds of α-amylases, and industrial application conditions of these kinds of α-amylases vary greatly depending on the characteristics of the desired products.

The α-amylase (α-1,4-glucan-4-glucanohydrolases, E.C. 3.2.1.1) is effective in hydrolyzing α-1,4 glycosidic bond in starch and other polysaccharides. In view of the demand for improving enzyme efficiency and reducing production cost during the hydrolysis of starch, the search for α-amylase which can support effective starch liquefaction in different application fields has become an important research direction in the academia and industry. At present, the improvements of the enzyme species by using enzyme engineering techniques mainly focus on the improvements of heat resistance, acid-base tolerance performance, and liquefaction effect.

Many α-amylases in plants and microorganisms have been found to have commercial values, mainly including *B. licheniformis* α-amylase, *B. amyloliquefaciens* α-amylase and *G. stearothermophilus* α-amylase, wherein the variants derived from *B. licheniformis* α-amylase (L-type) as a template are the most abundant and are most widely used.

SUMMARY OF THE INVENTION

In the present invention, in order to meet the needs of industrial production, we used *B. licheniformis* α-amylase (L-type) as a template to construct a series of new α-amylase variants, and improved the application efficiency of the enzyme species. Especially in the case of low pH and reduction in the amount added, the liquefaction efficiency of the α-amylase variants of the present invention can be comparable to that of the mainstream products in the market.

An object of the present invention is to provide a *B. licheniformis* α-amylase (L-type) variant, which can increase the liquefaction efficiency and can adapt to the needs of industrial production. In particular, the enzyme activity and other properties of the α-amylase variant of the present invention can be comparable to those of mainstream products in the market under the conditions of a temperature of 100° C. or above and a pH of 5.0-5.8.

Another object of the present invention is to provide a gene encoding the α-amylase variant.

Still another object of the present invention is to provide a method for producing the α-amylase variant and use thereof.

The objects of the present invention can be achieved by the following technical solutions:

An α-amylase variant, which is obtained by deleting the first N-terminal amino acid residue V from the α-amylase of *B. licheniformis* and replacing it with three other amino acid residues DGL.

A full length gene sequence encoding the α-amylase of *B. licheniformis*, which is set forth in SEQ ID NO: 1; and the corresponding amino acid sequence, which is set forth in SEQ ID NO: 2.

An amino acid sequence of the α-amylase variant, which is set forth in SEQ ID NO: 4.

A nucleotide sequence encoding the α-amylase variant, which is preferably set forth in SEQ ID NO: 3.

A gene encoding the α-amylase variant of the present invention.

Wherein the gene is preferably set forth in SEQ ID NO: 3.

An expression vector for expressing the α-amylase variant of the present invention, which comprises a gene encoding the α-amylase variant of the present invention.

Wherein, the expression vector comprises an expression cassette composed mainly of a natural or synthetic promoter sequence, a natural or synthetic ribosome binding site, a natural or synthetic terminator sequence, and the gene encoding the α-amylase variant of the present invention.

A recombinant cell for expressing the α-amylase variant of the present invention, which comprises one or more genes encoding the α-amylase variant of the present invention.

Wherein, the host cell of the recombinant cell is preferably selected from a *Bacillus* strain, further preferably *B. licheniformis* or a *Bacillus* strain genetically engineered to inactivate some endogenous proteins; most preferably *B. licheniformis* genetically engineered to inactivate AprE and/or Blase.

A method for producing the α-amylase variant of the present invention, which comprise the steps: culturing a recombinant cell containing a gene sequence encoding the α-amylase variant under conditions suitable for the expression of the α-amylase variant, and obtaining the α-amylase variant from the recombinant cell or its culture supernatant.

Use of the α-amylase variant of the present invention in the hydrolysis of α-1,4 glycosidic bonds of polysaccharides; preferably in the hydrolysis of α-1,4 glycosidic bonds of polysaccharides under conditions of high temperature and/or low pH.

Wherein, the high temperature is preferably 80° C. to 110° C., more preferably 100° C. to 110° C., and the low pH is preferably 5.0 to 5.8.

Beneficial Effects

A series of α-amylase variants provided by the present invention have high catalytic activity under an acidic condition of pH 5.0-5.8 and a high temperature of 100° C. or above. The acid resistance and thermal stability of these α-amylase variants are suitable for starch liquefaction.

SEQUENCE LISTING

Figure 1:
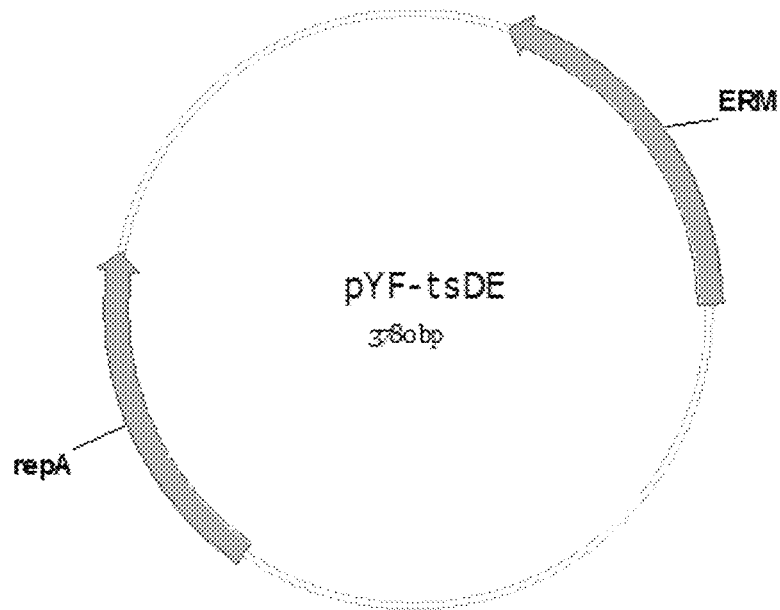
FIG. 1 shows a pYF-tsDE vector, which comprises a temperature-sensitive element (having replication activity at 30° C.) and an erythromycin determinant gene (ErmC), which can tolerate 300 μg/mL erythromycin in E. coli and 5 μg/mL erythromycin in B. licheniformis. The recombinant host cell containing the nucleotide sequence encoding the α-amylase variant was screened with erythromycin.

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. The Sequence Listing is submitted as an ASCII text file, created on May 25, 2018, 32 KB, which is incorporated by reference herein. In the accompanying sequence listing:

SEQ ID NOS: 1 and 2 show a full length gene sequence encoding the α-amylase of B. licheniformis, and the corresponding amino acid sequence, respectively.

SEQ ID NOS: 3 and 4 show a nucleotide sequence encoding an α-amylase variant and the corresponding amino acid sequence, respectively.

SEQ ID NO: 5 shows a synthetic promoter sequence.

SEQ ID NO: 6 shows a synthetic termination sequence.

SEQ ID NO: 7 shows a natural signal sequence.

SEQ ID NOS: 8 and 9 are forward and reverse primers for amplifying the upstream sequence of the Apr gene, respectively.

SEQ ID NOS: 10 and 11 are forward and reverse primers for amplifying the downstream sequence of the Apr gene, respectively.

SEQ ID NOS: 12 and 13 are forward and reverse primers for amplifying the upstream sequence of the Blase gene, respectively.

SEQ ID NOS: 14 and 15 are forward and reverse primers for amplifying the downstream sequence of the Blase gene, respectively.

SEQ ID NOS: 16 and 17 are forward and reverse primers for identifying AprE, respectively.

SEQ ID NOS: 18 and 19 are forward and reverse primers for identifying Blase, respectively.

DETAILED DESCRIPTION OF THE INVENTION

In the present invention, the term "α-amylase" refers to an enzyme capable of hydrolyzing the α-1,4 glycosidic bonds of polysaccharides. For example, α-amylase can hydrolyze starch to dextrins.

In the present invention, the term "parental α-amylase" refers to a natural α-amylase. The natural α-amylase is a bacterial α-amylase and includes, but is not limited to, Bacillus subtilis, B. licheniformis, B. amyloliquefaciens, G. stearothermophilus and Bacillus cereus.

According to a preferred embodiment of the present invention, the native α-amylase is derived from a Bacillus strain, especially B. licheniformis and G. stearothermophilus. The full-length encoding sequence of B. licheniformis is set forth in SEQ ID NO: 1, and the corresponding amino acid sequence is set forth in SEQ ID NO: 2.

In the present invention, the term "α-amylase variant" refers to a non-naturally occurring α-amylase obtained by addition, deletion, and/or substitution of one or several amino acid residues in the amino acid sequence of the parental α-amylase, while still retaining the ability of the parental to hydrolyze α-1,4 glycosidic bonds.

In the present invention, the term "liquefaction" generally refers to the process of breaking down carbohydrates into small molecule polysaccharides. When an α-amylase or α-amylase variant is added, "liquefaction" specifically refers to hydrolyzing the α-1,4 glycosidic bond of the carbohydrate.

In the present invention, the term "α-1,4 glycosidic bond" refers to a bond linking C1 of the preceding glucose with C4 of the latter glucose, that is, an α-1,4 glycosidic bond.

The present invention relates to an "α-amylase variant" obtained by sequence modification of a parental α-amylase. The parental α-amylase is a natural α-amylase, especially a bacterial native α-amylase. According to an embodiment of the present invention, an α-amylase variant is obtained by the mutation or deletion of one or several amino acid residues in the amino acid sequence of the parental α-amylase.

The present invention includes a series of α-amylase variants. According to an embodiment of the present invention, the homology of the amino acid sequences of the series of α-amylase variants is at least 95%, even 95%, 96%, 97%, 98%, 99% or 100%, respectively.

As an illustrative and non-limiting example of the present invention, the α-amylase variant is obtained by deleting the first N-terminal amino acid residue V from the α-amylase of B. licheniformis and replacing it with three other amino acid residues DGL. The amino acid sequence is set forth in SEQ ID NO: 4.

The α-amylase variant of the present invention retains the ability to hydrolyze the α-1,4 glycosidic bond. In addition, the performance of these α-amylases meet the requirements of industrial production, such as the improvement of liquefaction efficiency, and the stable catalytic activity at acidic pH or high temperature.

According to an embodiment of the present invention, an α-amylase variant is stable in catalytic activity at an acidic condition of pH 5.0 or at a temperature of 100° C. or above (especially at a temperature between 100° C. and 108° C.). The improved properties of the α-amylase variant are more amenable to the liquefaction reaction of the starch industry, because the liquefaction process in the starch industry is often carried out at low pH and high temperature conditions.

All α-amylase variants of the present invention can be used in liquefaction reaction. In a preferred embodiment, the α-amylase variant is derived from a parental α-amylase, in particular a parental α-amylase derived from B. licheniformis. In a particularly preferred embodiment, the amino acid sequence of the α-amylase variant is set forth in SEQ ID NO: 4 in the Sequence Listing.

According to the present invention, any carbohydrate containing α-1,4 glycosidic bond can be used in the liquefaction reaction. Carbohydrates containing one or more α-1,4 glycosidic bonds include but are not limited to starch, amylopectin, amylose, and dextran.

Many carbohydrates contain α-1,6-glycosidic bonds and α-1,4-glycosidic bonds, such as amylopectin. The term "α-1,4-glycosidic bond" refers to a bond linking C1 of the preceding glucose with C4 of the latter glucose, that is, an α-1,4 glycosidic bond. Therefore, the α-amylase variant of the present invention can be used in conjunction with a pullulanase capable of hydrolyzing α-1,6 glycosidic bonds during saccharification. Enzymes capable of hydrolyzing α-1,4 glycosidic bonds include, but are not limited to, α-amylases. In a preferred embodiment of the present invention, the enzyme that catalyzes the hydrolysis of α-1,4 glycosidic bonds is an α-amylase.

Therefore, according to an embodiment of the present invention, a method for further catalyzing the saccharification reaction to increase the efficiency is to use pullulanase in combination. In the present invention, the term "pullulanase" refers to a hydrolase capable of hydrolyzing α-1,6 glycosidic bonds.

In the present invention, the use of α-amylase and pullulanase in combination in the saccharification of starch can increase the purity of glucose and maltose. In addition, the use of the aforementioned complex enzyme in the saccharification reaction can effectively reduce the substrate concentration, increase the conversion efficiency, and can also have a higher catalytic activity at an acidic pH or higher temperature, and can be more adapted to industrial conditions for hydrolyzing starch.

The present invention provides a method in which an α-amylase variant can hydrolyze α-1,4 glycosidic bonds for saccharification under any temperature and pH conditions suitable for industrial production. According to the present invention, the liquefaction reaction can be carried out at a high temperature of 80° C. to 110° C., such as 80° C., 90° C., 100° C., 105° C., and 110° C. The saccharification reaction can also be carried out under an acidic pH condition of pH 5.0 to pH 5.8, such as pH 5.0, 5.2, 5.4, 5.6, and 5.8.

According to an embodiment of the present invention, the liquefaction reaction catalyzed by the α-amylase variant has stable activity under conditions of acidic pH and a temperature of 100° C. or above.

In another aspect, the expression vector of the present invention comprises a synthetic nucleotide sequence encoding an α-amylase variant, and a recombinant host cell comprises the above expression vector. The expression vector comprises a synthetic nucleotide sequence encoding different α-amylase variants. The expression vector can be integrated into the genome of the host cell. For example, the expression vector comprises the synthetic nucleotide sequence SEQ ID NO: 3.

The expression vector of the present invention preferably comprises a natural or synthetic promoter sequence, a natural or synthetic ribosome binding site, a natural or synthetic terminator sequence. These genetic elements together with the encoding sequence of the synthetic α-amylase variant constitute an expression cassette, which constitutes an expression vector together with a vector backbone. For example, the expression vector comprises an expression cassette, which includes the following elements: a promoter sequence, a synthetic ribosome binding site, a synthetic nucleotide sequence encoding an α-amylase variant of the present invention and a terminator sequence. A signal sequence is capable of directing the secretion of the α-amylase variant, and the introduction of the signal sequence into the expression vector or expression cassette, especially the introduction of the signal sequence upstream of the initiation codon is more advantageous for the secretion of the α-amylase variant.

According to a preferred embodiment of the present invention, the expression vector is suitably expressed in bacteria, in particular a Bacillus strain, and more preferably expressed in B. licheniformis. In a particularly preferred embodiment, the expression vector can be integrated into the genome of Bacillus, in particular the genome of B. licheniformis. Expression vectors for host cells that can be used for integration of polynucleotide sequences in chromosomes, and methods for constructing such expression vectors, are well-known common skills in the field of contemporary biology.

According to an embodiment of the present invention, the recombinant host cell may be genetically engineered to comprise a nucleic acid sequence comprising one or more α-amylase variant gene expressions. Any technique can be used to genetically engineer a host cell to comprise one or more synthetic nucleic acid sequences encoding the α-amylase variant of the present invention, e.g., chromosomal integration. Vectors containing temperature-sensitive origins and resistance selection markers can be used for the integration step. These vectors are integrated with a specific region of the genome through the Campbell mechanism, and recombinant strains are obtained through resistance screening. The resistance screening markers of the recombinant strains are removed by homologous recombination during the subsequent cultivation.

According to an embodiment of the present invention, the recombinant host cell has been engineered to inactivate some endogenous proteins. The endogenous proteins that can be inactivated include, but are not limited to, extracellular proteases. The recombinant host cell inactivates some of the endogenous proteins either before or after transformation of the nucleic acid sequence containing the α-amylase variant expression gene. A more suitable method is to inactivate the exogenous secreted protease of the host bacterium before transferring the vector expressing the α-amylase variant gene.

First, B. licheniformis has been modified to inactivate some exogenous protease genes. In particular, B. licheniformis strain can inactivate some extracellular proteases, such as subtilisin (AprE), glutamic acid-specific protease (Blase). The genetic engineering makes the B. licheniformis strain more suitable for the expression and secretion of α-amylase variants.

The present invention provides a method for producing an α-amylase variant. According to an embodiment of the present invention, the method comprises culturing a recombinant host cell containing a nucleotide sequence encoding an α-amylase variant under conditions suitable for the expression of an α-amylase variant and obtaining the α-amylase variant from the recombinant host cell or its supernatant.

All recombinant host cells of the present invention are capable of producing α-amylase variants. The recombinant host cell comprises at least one copy of a nucleotide sequence encoding an α-amylase variant. These nucleotide sequences encoding α-amylase variants are capable of expressing α-amylase variants under suitable conditions. The α-amylase variants secreted from recombinant host cells can be collected from recombinant cells or supernatants. The collection methods include but are not limited to filtration, centrifugation, and the like.

According to an embodiment of the present invention, the α-amylase variant can be highly produced by fermentation of genetically engineered *B. licheniformis*. The nucleotide sequence encoding the α-amylase variant is introduced into *B. licheniformis* by genetic engineering. More preferably, *B. licheniformis* of the present invention has been removed the resistance screening gene and is environmentally friendly, and the produced α-amylase variant is more suitable for use in the food industry.

The following examples of the present invention further illustrate the essence of the present invention. It should be understood that the following examples do not limit the present invention, and the scopes of the present invention are determined by the appended claims.

EXAMPLES

Example 1

Construction of pYF-tsDE plasmid pYF-tsDE (FIG. 1) is a thermosensitive *E.coli/B. licheniformis* shuttle plasmid. The plasmid consists of a temperature-sensitive origin of replication (active at 30° C.) and an erythromycin resistance gene (ErmC), the resistance of which is 300 μg/ml in *E. coli*, and 5 μg/ml in *B. licheniformis*. At 37° C., the replication origin on the plasmid is inactivated and the plasmid is integrated into the specified site of the host genome and screened with ErmC.

Figure 2:
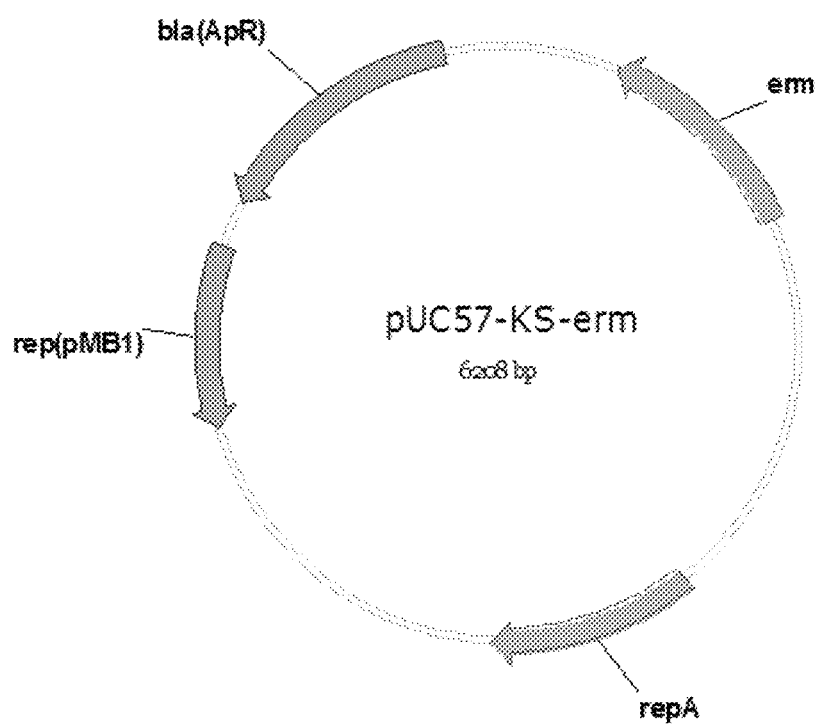
FIG. 2 is a schematic diagram of a pUC57-KS-erm vector from which the pYF-tsDE vector of the present invention can be obtained.

The pYF-tsDE plasmid was constructed by digesting the plasmid pUC57-KS-erm (synthesized by Genscript with commission, and the sequence was shown in CN 104073458A, FIG. 2) with BglII, recovering, purifying a 3.8 kbp fragment and self-ligating with T4 ligase (New England Biolabs), and the cloned plasmid was pYF-tsDE. Transformants were propagated in *E. coli* TOP10 and served as the backbone for all of the following gene manipulations.

Example 2

Construction of a Protease Deficient *B. licheniformis* Strain

Genetically engineered strains that are host cells for recombinant enzyme products have been reported in the literature (Widner et al., Journal of Industrial Microbiology & Biotechnology, 25, 204-212, 2000). These recombinant host cells typically contain one or more nucleic acid structures encoding a target sequence for expression by an enzyme. In the present invention, *B. licheniformis* is used as a genetically manipulated recipient bacteria. The transformation of *Bacillus* can now be achieved through very mature means such as competent cell transformation, electrotransformation and protoplast transformation (Young et al., J Bacteriology, 81, 823-829, 1961; Shigekawa et al., Biotechniques, 6, 742-751, 1988; Chang et al., Molecular General Genetics, 168, 111-115, 1979).

In the present invention, a single expression cassette for α-amylase variant comprises a natural or synthetic promoter sequence, a signal peptide sequence screened from *Bacillus*, a synthetic ribosome binding site, and an α-amylase variant encoding gene from *B. licheniformis*, and a transcription terminator. Such a design would greatly enhance the level of gene expression in the host strain and the secretion amount of the α-amylase variant. Substitution of the α-amylase variant encoding gene for a specific site on the genome of the *B. licheniformis* cell was achieved by plasmid-mediated single cross-homologous recombination.

In *B. licheniformis*, the activities of extracellular proteases are detrimental to the secretion of heterologous enzymes. Two major extracellular proteases have been identified: subtilisin (AprE) and glutamic acid-specific protease (Blase). Most of the extracellular protease activities in *B. licheniformis* originate from these two proteases.

In the present invention, in order to obtain the structural integrity of the expression of the α-amylase variant gene, the above two genes were inactivated, and the continuous cross single Campbell type mechanism was adopted. The specific operation was as follows:

2.1 pYF-tsDE was digested by BglII and treated with OP to inhibit self-ligation;

2.2 Gene Knockout (1) In order to obtain each gene deletion fragment, a homologous sequence of approximately 500 bp was amplified from each side of the gene to be deleted by PCR using the genomic DNA of *B. licheniformis* as a template. *Bacillus subtilis* was pre-denatured at 98° C. for 5 minutes and could be used directly as a genomic DNA template in a PCR reaction.

The primers used for the PCR reaction were synthesized by Genscript. The primer sequences are as follows:

The primers for amplifying the upstream sequence of the Apr gene were:

```
lichApr_F1
                                     (SEQ ID NO: 8)
TTATTGAGCGGCAGCTTCGACATTGATCAGACCTT lichApr_R1
                                     (SEQ ID NO: 9)
CCTTACGGCATTCCTCTCAACAGCGGATCTTCAG
```

The primers for amplifying the downstream sequence of the Apr gene were:

```
lichApr_F2
                                    (SEQ ID NO: 10)
CCTGAAGATCCGCTGTTGAGAGGAATGCCGTAAGG lichApr_R2
                                    (SEQ ID NO: 11)
ATGATGAGGAAAAAGAGTTTTTGGCTTGGGATGCTGAC
```

The primers for amplifying the upstream sequence of the Blase gene were:

```
blalich_F1
                                         (SEQ ID NO: 12)
TTATTGTGCGCTGTTTTTCCAGTTGGTCAAATTGTCG blalich_cR1
                                         (SEQ ID NO: 13)
CGGACAAGGGTCACCAACGGGACAACTGTTACCATC
```

The primers for amplifying the downstream sequence of the Blase gene were:

```
blalich_cF2
                                         (SEQ ID NO: 14)
GATGGTAACAGTTGTCCCGTTGGTGACCCTTGTCC blalich_R2
                                         (SEQ ID NO: 15)
CGGCGTTGGTTAGTAAAAAGAGTGTTAAACGAGGTTTGAT
```

The PCR amplification system was 50 µl and the reaction procedure was as follows:

(1) *Bacillus subtilis, B. licheniformis* 14580 monoclone pre-denatured at 98° C. for 8 minutes;
(2) 96° C., 15 seconds;
(3) 58° C., 15 seconds;
(4) 72° C., 30 seconds; repeated steps 2-4 for 25-30 times;
(5) Final extension at 72° C., 2 minutes.

The PCR product was detected by 0.8% agarose gel electrophoresis and purified using an Axygen kit.

2.3 Overlap extension PCR method to amplify the target gene with sequence deletion of about 400-500 bp The internal gene deletion fragment was obtained using overlap extension PCR (SOE). The specific operation was as follows:

(1) The upstream and downstream PCR fragments of each gene in 2.2 were recovered and purified; (2) Using a 1:1 molar ratio of the upstream and downstream homologous fragments of each gene of interest as template, PCR amplification was performed using primers XX-CZ-F1 and XX-CZ-R2 ("XX" for Apr or Blase) to obtain the AprE gene or Blase gene with internal fragments deleted.

The fragments were then recombined into the BglII-linearized pYF-tsDE vector using the Clone-EZ Cloning Kit (provided by Genscript) and the resulting recombinant plasmids were named: pYF-tsDE-Apr and pYF-tsDE-Blase. These recombinant plasmids were temperature-sensitive plasmids, and the Apr gene or Blase gene contained therein lacks an internal sequence of about 400-500 bp with respect to the entire gene, respectively.

Replacement of different alleles can be achieved by homologous recombination. The method can be referred to CN102124112A, and other well-known methods of homologous recombination in the art can also be used.

2.4 Plasmid Transformation

This experiment used a method of transforming knockout plasmids into competent cells of *B. licheniformis*, and the screening process was as follows:

(1) The thermosensitive plasmid pYF-tsDE-Apr or pYF-tsDE-Blase was used to transform *B. licheniformis* (CICC 22794, purchased from China Center of Industrial Culture Collection) competent cells;
(2) Positive clone strains were screened with erythromycin (5 µg/ml) resistance on LB (10 g peptone, 5 g yeast extract, 10 g sodium chloride per liter) medium at 30° C.;
(3) The positive clones were then transferred to condition of 37° C. for incubation, allowing the temperature-sensitive plasmid to be fused to the host genome. In order to replace the gene in the set position, several clones were selected and inoculated in 2×YT medium for 24 hours, and then subcultured once. The whole process was subcultured for 4-5 times (generally 5-7 days).

(4) Erythromycin-sensitive *Bacillus subtilis* cells were screened for PCR identification. The transparent hydrolyzed circle can be observed with a 1% skim milk LB plate at the same time. The knockout strain should show a significantly reduced hydrolysis circle.

```
PCR primers used in the identification:
AprE: Apr-seqF1/Apr-seqR3
Blase: Blase-seqF1/Blase-seqR3

Apr-seqF1:
                                         (SEQ ID NO: 16)
GCCAGGTTGAAGCGGTCTATTCAT Apr-seqR3:
                                         (SEQ ID NO: 17)
TACGGCCATCCGACCATAATGGAAC Blase-seqF1:
                                         (SEQ ID NO: 18)
GAAGAGCCGGTCACAATTGC Blase-seqR3:
                                         (SEQ ID NO: 19)
GGCCGTTAGATGTGACAGCC
```

Example 3

Integration and Construction of α-Amylase Variant Strain 3.1 Construction of amylase Expression Cassettes The integration plasmid was constructed using the same method as the pYF-tsDE plasmid described above. In order to integrate the expression cassette into the designed AmyE site on the genome, a homologous region of about 800 bp was respectively designed upstream and downstream of the AmyE site on the genome and ligated on both sides of an α-amylase variant expression cassette. At the same time, a number of completely naturally selected bacterial chromosomal DNA fragments and functional synthetic sequences were assembled, which were necessary for controlling the expression of the α-amylase variant gene.

Figure 3:
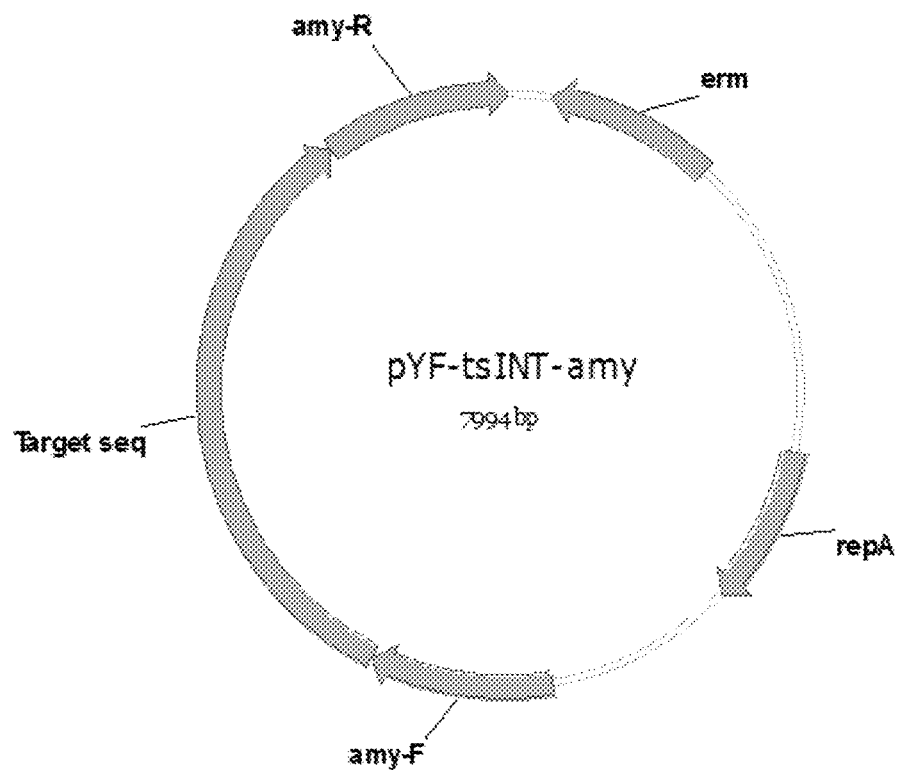
FIG. 3 is a schematic representation of a pYF-tsINT-amy vector.

A typical amylase expression cassette consists of the following components. A typical α-amylase variant expression cassette consists of the following elements: a natural or synthetic promoter sequence (SEQ ID NO: 5), a synthetic ribosome binding site aaaggagg, an α-amylase variant encoding gene derived from *B. licheniformis* (SEQ ID NO: 3, respectively) and a synthetic termination sequence (SEQ ID NO: 6). A strong natural signal sequence (SEQ ID NO: 7) selected from *Bacillus subtilis* was inserted upstream of the promoter of the α-amylase variant encoding gene to enhance the secretion efficiency of the expressed enzyme. The complete α-amylase variant expression cassette was inserted into the BglII site in the linearized pYF-tsDE using the Clone-EZ Cloning Kit (Genscript). The resulting temperature-sensitive integration plasmid was named pYF-tsINT-amy (FIG. 3). The synthesis of the above sequence was performed by Genscript, and the above sequences were sequentially tandemly connected to obtain an α-amylase enzyme expression cassette. The signal peptide sequences in this framework were screened from Bacillus subtilis and can effectively increase the secretion of α-amylase.

3.2 Plasmid Transformation

The entire α-amylase expression cassette (including homologous segments upstream and downstream of the amyE gene) was circularized using a recombinant technique to cyclize the BglII-linearized pYF-tsDE plasmid (recombination kit provided by Genscript), and the constructed thermosensitive plasmid was named as pYF-tsINT-amy. The plasmid was used for transformation into *Bacillus licheniformis* with deletion of the AprE and Blase protease genes (CICC 22794, purchased from China Center of Industrial Culture Collection), and the α-amylase variant expression cassette without resistance maker was going to replace AmyE. Using the method described above, a strain that successfully integrated the α-amylase variant encoding gene into the chromosome of *B. licheniformis* produced a transparent circle on the blue starch plate, and PCR further validated that the expression cassette was integrated in the AmyE site of the recipient strain.

*B. licheniformis* engineered strain that produces α-amylase variants was stored at −80° C.

Example 4

Shake Flask Fermentation of α-Amylase Variant Production

An activated bacterial monoclone (containing the α-amylase variant expression cassette) was inoculated into 20 ml medium (containing maltose syrup 4.0%, peptone 2.0%, yeast powder 0.1%, $KH_2PO_4$ 0.6% and corresponding antibiotics) to log phase. 1.2 ml of the culture solution was inoculated into 30 ml medium (containing maltose syrup 12.0%, peptone 1.0%, yeast powder 1%, $KH_2PO_4$ 0.2%, $MnCl_2$ 0.003%), and cultured on a reciprocating shaker at 120 rpm for 3 days. Samples were taken at 24 hours, 48 hours and 72 hours, respectively, and centrifuged at 1000 rpm for 1 minute. The supernatant was stored and analyzed by SDS-PAGE. The α-amylase variant had a molecular weight of about 53 kD.

The α-amylase variant activity was measured as described in Example 6.

Example 5

Step-Feeding Fermentation Process for α-Amylase Variant

The genetically engineered *B. licheniformis* strain cryopreserved at −80° C. obtained in Example 3 was streaked on an agar slant, and cultured overnight at 37° C. The agar slant formula was as follows: peptone 1%, yeast extract 0.5%, NaCl 1%, agar powder 2%.

First, several fresh clones were selected and cultured in a seed shake flask containing 50 ml of culture medium at 37° C. for 16 hours. Seed shake flask formulation: maltose syrup 4.0%, peptone 2.0%, yeast extract 0.1%, $KH_2PO_4$ 0.6%. After 16 hours, all the seed broths were transferred to a 7 L stainless steel fermenter containing 4 L of culture medium and the fermentation was continued for 12 hours at agitation speed of 350 rpm and an aeration rate of 650 L/H. Fermenter formula: malt syrup 6.0%, peptone 1.0%, yeast extract 1%, $KH_2PO_4$ 0.2%, $MnCl_2$ 0.003%. The fermentation pH was then controlled at about 5.7±0.2 with 5% phosphoric acid and the fermentation tank was continuously fed at a rate of 1 L/18 hrs in the first 18 hours and at a rate of 0.5 L/18 hrs for the next 110 hours. The feed formulation was as follows: maltose syrup 48%, peptone 6%, yeast extract 8%. The entire fermentation process lasted 140-150 hours. All media in the fermenter were collected and centrifuged at 4° C., 1010 krpm for 30 minutes. The supernatant after centrifugation was used for α-amylase variant enzymatic activity analysis.

Example 6

Amylase Activity Assay

The amylase activity assay was performed using Bestzyme amylase unit (BAU). One BAU is defined as the amount of enzyme required to liquefy 1 mg of soluble starch in one minute at pH 6.0 and 70° C.

Briefly, the enzyme activity was determined as follows: 20 ml of 20 g/L soluble starch solution was mixed with 5 ml of phosphate buffer pH 6.0, preheated at 70° C. for 8 min, then 1.0 ml of diluted enzyme solution was added, and the reaction was accurately performed for 5 minutes. 1 ml of the reaction solution was added to a test tube containing 0.5 ml of 0.1 mol/L hydrochloric acid solution and 5 ml of dilute iodine solution in advance, and shaken well. With 0.5 ml 0.1mol/L hydrochloric acid solution and 5 ml dilute iodine solution as blanks, the absorbance value was quickly measured at a wavelength of 660 nm, and the enzymatic activity of the test sample was obtained by checking the table according to the absorbance.

Example 7

Applications of Amylase

Unless otherwise stated, 1 BAU: the amylase activity assay was performed using Bestzyme amylase unit (BAU). One BAU is defined as the amount of enzyme required to liquefy 1 mg of soluble starch in one minute at pH 6.0 and 70° C.

tDS: dry matter per ton

Figure 4:
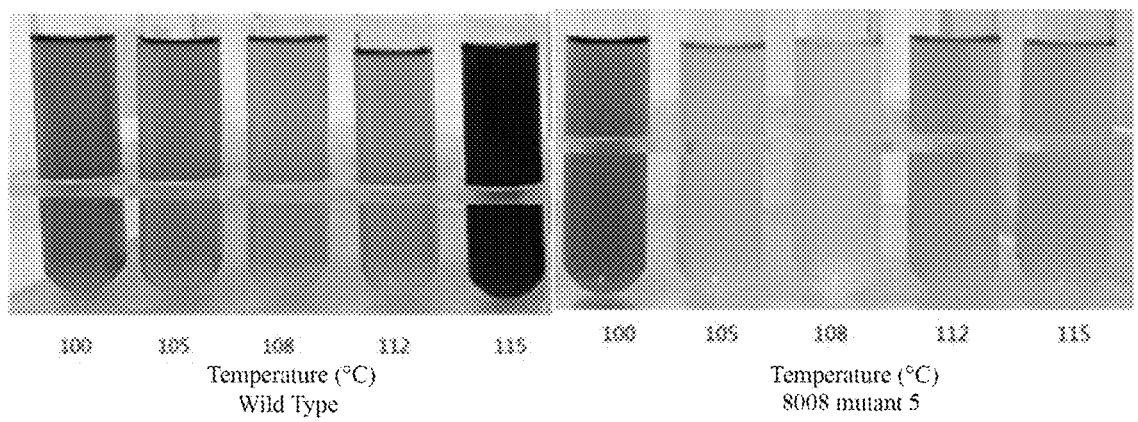
FIG. 4 shows a comparison of amylase liquefactions at different jetting temperatures.

The amylase variant expressed and isolated from *Bacillus licheniformis* cells was first subjected to a first round of liquefaction test using corn starch. Test conditions: 18 Baume degrees (°Bé), well-mixed, pH adjusted to 5.2 with hydrochloric acid. 0.4 kg/tDS of amylase was added, and the injection temperature was 100, 105, 108, 112, and 115° C., respectively, maintained for 5-8 min followed by flashing and maintained at 95° C. for 120 min. After liquefaction, DE and iodine test were performed, and protein flocculation and viscosity were observed. The wild type was used as a control, and the results are shown in Table 1 and FIG. 4.

TABLE 1

Comparison of amylase liquefactions at different jetting temperatures

| Temperature (° C.) | Wild type DE (%) | 8008 mutant 5 DE (%) |
|---|---|---|
| 100 | 18.02 | 19.77 |
| 105 | 17.79 | 19.47 |
| 108 | 15.00 | 17.48 |
| 112 | 13.85 | 18.72 |
| 115 | 7.05 | 13.91 |

The results showed that 8008 mutant 5 (i.e., the α-amylase variant of the present invention prepared as described above) was significantly better than the wild type. As the 8008 mutant at different jetting temperatures, the liquefaction at 108° C. was overdone; the liquefaction at 112° C. was appropriate, and the protein flocculation was good; the liquefaction at 115° C. was still good and the protein flocculation was normal, indicating that the α-amylase variant of the present invention has very good heat resistance, while the wild type cannot tolerate high temperature of 115° C.

Figure 5:
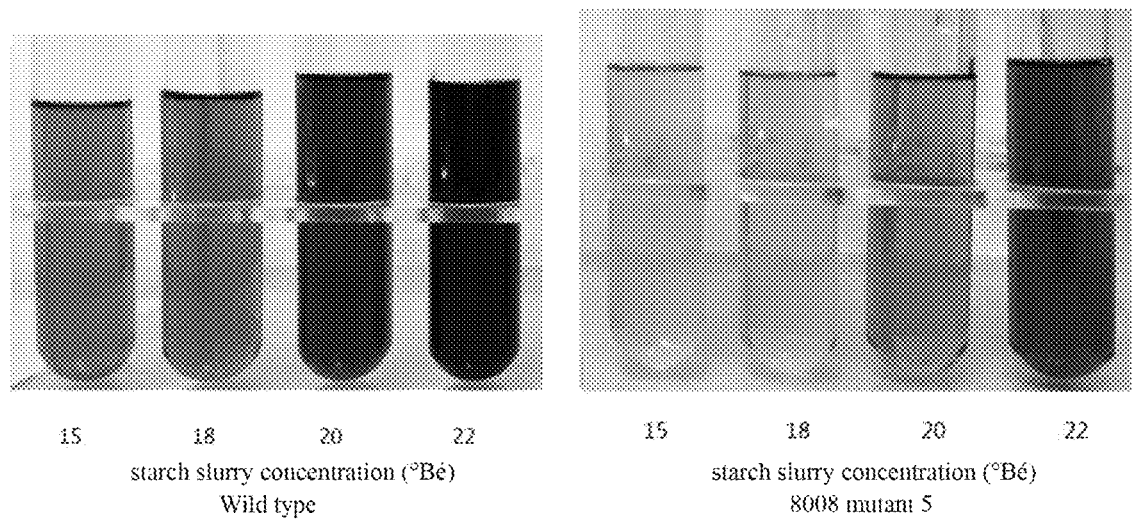
FIG. 5 shows a comparison of amylase liquefactions with different concentrations of starch slurry.

Secondly, we tested the resistance of amylase to high substrate concentration by liquefaction experiments with different starch slurry concentrations. The liquefaction conditions were the same as those described above, and the injection temperature was 108° C. The wild type was used as a control, and the results are shown in Table 2 and FIG. 5.

TABLE 2

Comparison of amylase liquefactions with different concentrations of starch slurry

| Baume degree (°Bé) | Wild type DE (%) | 8008 mutant 5 DE (%) |
|---|---|---|
| 15 | 15.27 | 18.75 |
| 18 | 15.04 | 18.62 |
| 20 | 14.98 | 18.53 |
| 22 | 12.49 | 16.94 |

As shown in Table 2, 8008 mutant 5 was significantly better than the wild type. As the 8008 mutant with different starch slurry concentrations, the α-amylase variant of the present invention could still normally liquefy when the concentration of the starch slurry was as high as 22°Bé, indicating that the α-amylase variant of the present invention could be used for thick slurry liquefaction, thereby effectively saving factory costs.

Figure 6:
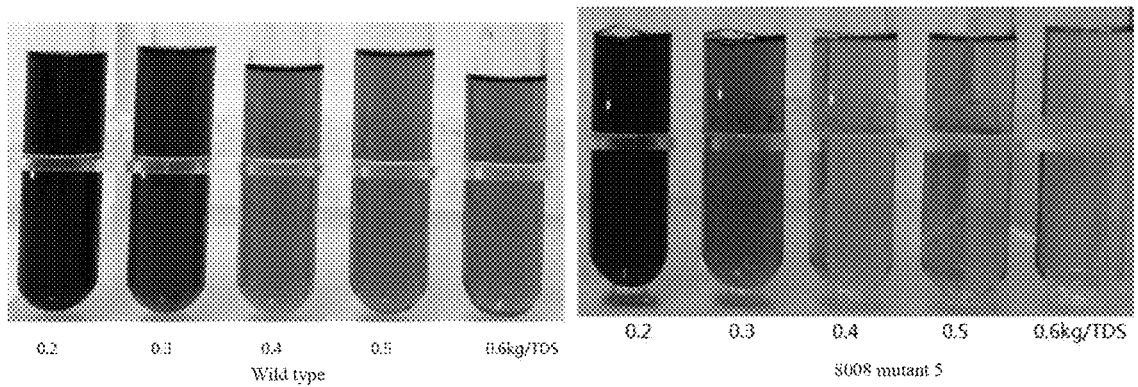
FIG. 6 shows a comparison of amylase liquefactions with different amounts of enzyme added at pH 5.0.

Then, we measured the acid resistance of the amylase and performed liquefaction with different amounts of enzyme added. The liquefaction reaction conditions were as described above, the pH was 5.0, and the amount of enzyme added was 0.2, 0.3, 0.4, 0.5, and 0.6 kg/tDS, respectively. The wild type was used as a control, and the results are shown in Table 3 and FIG. 6.

TABLE 3

Comparison of amylase liquefactions with different amounts of enzyme added at pH 5.0

| Amount of enzyme added (kg/tDS) | Wild type DE (%) | 8008 mutant 5 DE (%) |
|---|---|---|
| 0.2 | 8.24 | 11.35 |
| 0.3 | 11.61 | 15.66 |
| 0.4 | 14.98 | 18.29 |
| 0.5 | 15.16 | 18.47 |
| 0.6 | 16.77 | 20.15 |

As shown in Table 3, 8008 mutant 5 was significantly better than the wild type. With 8008 mutant 5 under low pH with addition of 0.2-0.3 kg/tDS, the L-type amylase variant was still able to liquefy, indicating that the L-type amylase variant was highly tolerant to low pH, at the same time, under condition of small amount of enzyme added of 0.2 kg/tDS, the α-amylase variant of the present invention was still able to normally liquefy, which could effectively reduce the cost for enzyme used in factories.

In addition, we performed a test for the effect of amylase on saccharification and compared it with liquefaction solutions liquefied with the wild type amylase and Liquozyme Supra (purchased from Novozymes). Test conditions: 32% dry matter (DS), well-mixed, pH adjusted to 4.3 with hydrochloric acid. 0.45 kg/tDS complex glucoamylase was added and the reactions of 200 ml were conducted at 60° C. for 24 and 48 hours, respectively. Samples were filtered by 0.22 um membrane and inactivated at 100° C. for HPLC analysis. The results are shown in Table 4.

TABLE 4

Effect of amylase on saccharification

| | Glucose % | |
|---|---|---|
| Amylase | 24 hrs | 48 hrs |
| 8008 amylase mutant 5 | 94.53 | 96.36 |
| Wild type | 93.53 | 95.64 |
| Liquozyme Supra | 094.47 | 96.41 |

As shown in Table 4, using the liquefaction solution of the α-amylase variant of the present invention and the liquefaction solution of the Wild type, the saccharification effect of the α-amylase variant of the present invention was significantly better than the Wild type. Meanwhile, the liquefaction solution of the α-amylase variant of the present invention and the liquefaction solution of Liquozyme Supra had the same saccharification effect, indicating that the α-amylase variant of the present invention could be applied to the starch sugar industry.

Figure 7:
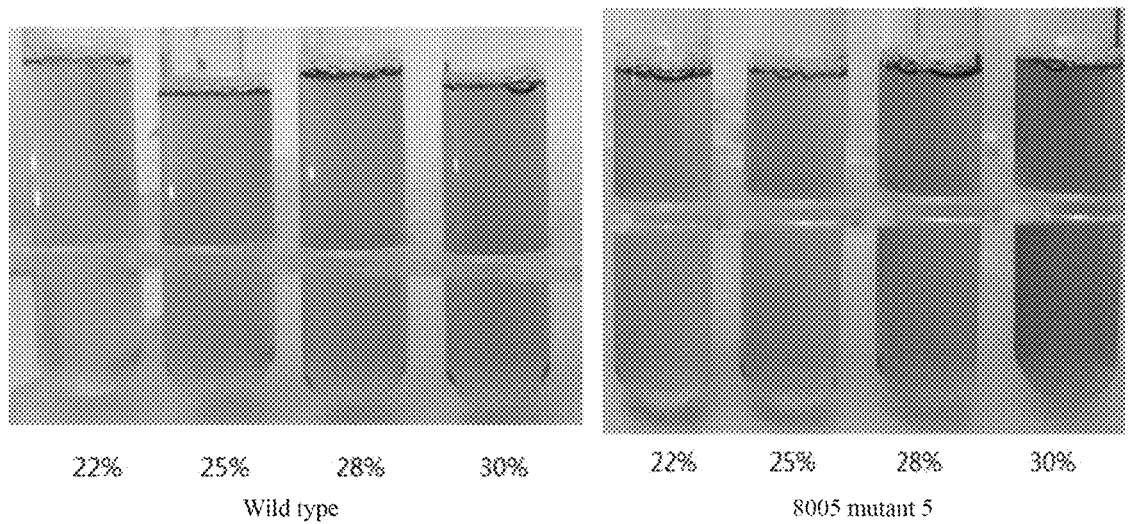
FIG. 7 shows a comparison of amylase liquefactions with different substrate concentrations.

Furthermore, we tested the effects of amylase on wheat starch. Test conditions: different substrate concentrations of 22, 25, 28, 30% (W/W), well-mixed, pH adjusted to 5.6 with hydrochloric acid. 0.4 kg/tDS amylase was added and maintained at 91-95° C. for 120 min. After liquefaction, DE and iodine test were performed, and protein flocculation and viscosity were observed. The wild type was used as a control, and the results are shown in Table 5 and FIG. 7.

TABLE 5

Comparison of amylase liquefactions with different substrate concentrations

| Concentration of substrate (%) | Wild type DE (%) | 8008 mutant 5 DE (%) |
|---|---|---|
| 22 | 20.85 | 21.61 |
| 25 | 20.21 | 20.29 |
| 28 | 19.64 | 19.71 |
| 30 | 18.14 | 19.48 |

The results showed that the 8008 mutant 5 was similar to the wild type result. With different substrate concentrations, the liquefaction at 22-25% was appropriate, and the protein flocculation was good; the liquefaction at 28 and 30% was still good, and protein flocculation was normal, indicating that the α-amylase variant of the present invention could be used for thick slurry liquefaction, thereby effectively saving factory costs.

Figure 8:
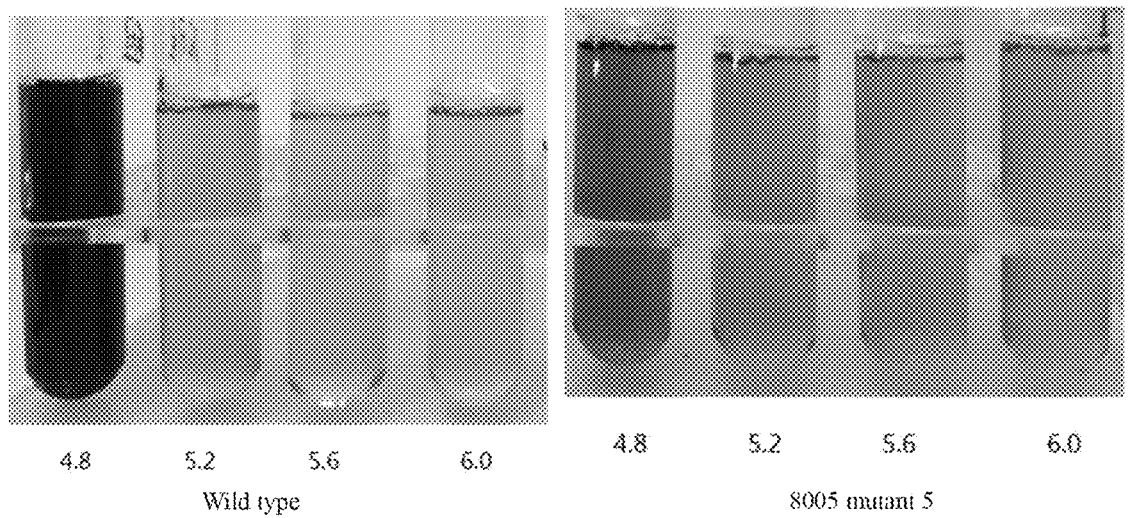
FIG. 8 shows a comparison of amylase liquefactions under different pH conditions.

Next, we measured the acid resistance of amylase and tested the liquefaction performance under different pH conditions. The liquefaction conditions were the same as those described above. The pH was 4.8, 5.2, 5.6, and 6.0, respectively, and the amount of enzyme added was 0.4 kg/tDS. The wild type was used as a control, and the results are shown in Table 6 and FIG. 8.

TABLE 6

Comparison of amylase liquefactions under different pH conditions

| pH | Wild type DE (%) | 8008 mutant 5 DE (%) |
|---|---|---|
| 4.8 | 8.11 | 14.45 |
| 5.2 | 20.43 | 19.76 |

TABLE 6-continued

Comparison of amylase liquefactions under different pH conditions

| pH | Wild type DE (%) | 8008 mutant 5 DE (%) |
|---|---|---|
| 5.6 | 21.77 | 20.30 |
| 6.0 | 21.97 | 21.10 |

As shown in Table 6, under the condition of pH 4.8, the α-amylase variant of the present invention was still able to normally liquefy, indicating that the α-amylase variant of the present invention had strong tolerance to low pH, and the wild type could not tolerate low pH.

Figure 9:
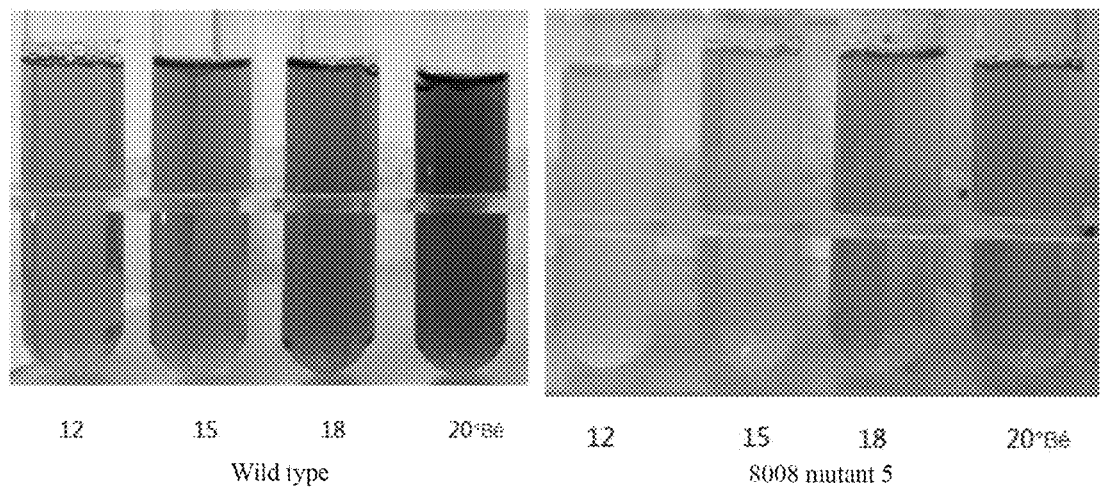
FIG. 9 shows a comparison of amylase liquefactions with different substrate concentrations.

Subsequently, we tested the effect of amylase on rice. The test conditions: different substrate concentrations of 12, 15, 18, 20 Baume degrees (°Bé), well-mixed, pH adjusted to 5.2 with hydrochloric acid. 0.4 kg/tDS of amylase was added, and the injection temperature was 108° C., maintained for 5-8 min followed by flashing and maintained at 95° C. for 120 min. After liquefaction, DE and iodine test were performed, and protein flocculation and viscosity were observed. The wild type was used as a control, and the results are shown in Table 7 and FIG. 9.

TABLE 7

Comparison of amylase liquefactions with different substrate concentrations

| Concentration of substrate (°Bé) | Wild type DE (%) | 8008 mutant 5 DE (%) |
|---|---|---|
| 12 | 19.53 | 22.93 |
| 15 | 18.87 | 21.75 |
| 18 | 17.06 | 21.46 |
| 20 | 15.72 | 20.89 |

The results showed that 8008 mutant 5 was significantly better than wild type. With 8008 mutant 5 at different substrate concentrations, the liquefaction at 12-18 °Bé was appropriate, and the protein flocculation was good; the liquefaction at 20 °Bé was still good and the protein flocculation was normal, indicating that the α-amylase variant of the present invention could be used for thick slurry liquefaction, thereby effectively saving factory costs.

Figure 10:
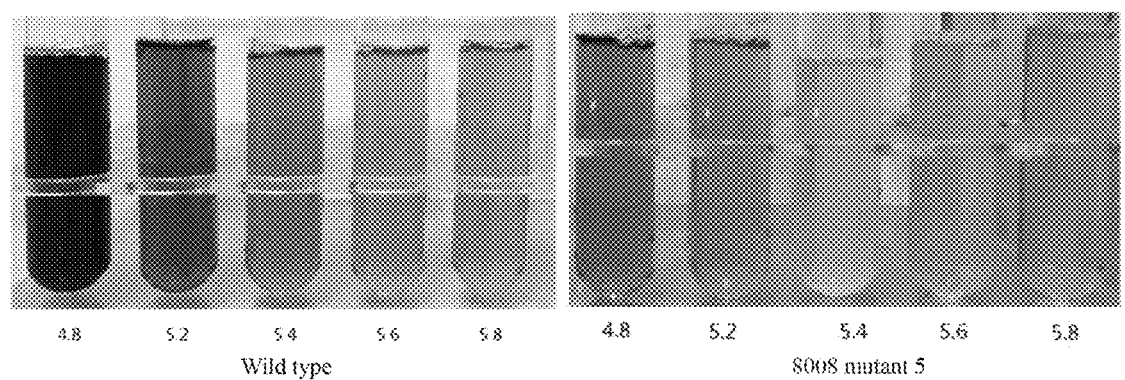
FIG. 10 shows a comparison of amylase liquefactions under different pH conditions.
Figure 11:
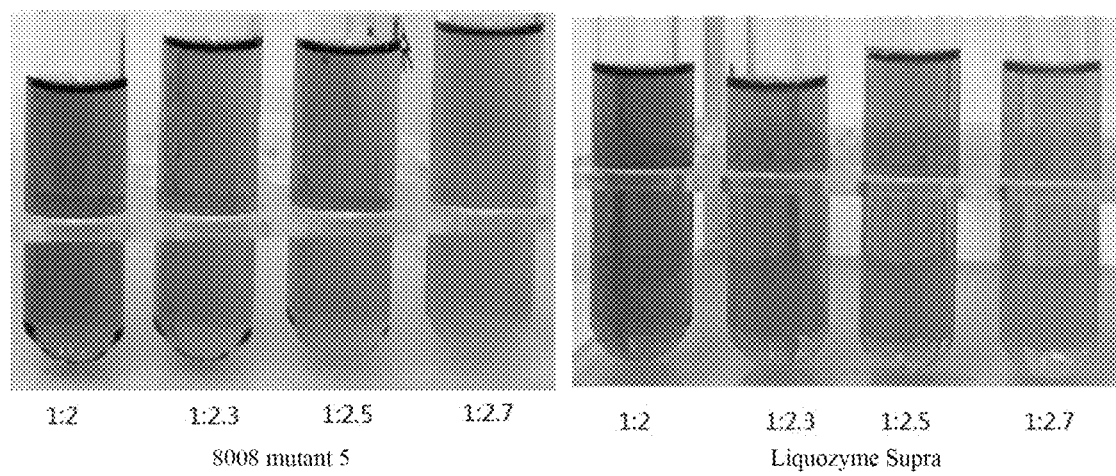
FIG. 11 shows a comparison of applications of amylases in corn alcohol liquefaction.

Next, we measured the tolerance of amylase to high substrate concentration by liquefaction experiments under conditions of different starch pH 4.8, 5.2, 5.4, 5.6, and 5.8. The liquefaction conditions were the same as described above, the injection temperature was 108° C., and the amount of enzyme added was 0.4 kg/tDS. The wild type was used as a control, and the results are shown in Table 8 and FIG. 10.

TABLE 8

Comparison of amylase liquefactions under different pH conditions

| pH | Wild type DE (%) | 8008 mutant 5 DE (%) |
|---|---|---|
| 4.8 | 7.46 | 16.17 |
| 5.2 | 16.89 | 20.33 |
| 5.4 | 17.42 | 20.79 |
| 5.6 | 17.96 | 21.35 |
| 5.8 | 18.44 | 21.81 |

As shown in Table 8, under conditions of pH 4.8 to 5.8, the α-amylase variant of the present invention was still able to normally liquefy, indicating that the α-amylase variant of the present invention had a strong tolerance to low pH, while the wild type had poor acid resistance.

Finally, because amylase has important applications in the alcohol industry, we also tested the liquefaction effect of amylase on alcohol production. Corn flour (40 mesh) with different ratios of feed to water was prepared, the pH was adjusted to 5.8 with hydrochloric acid, and 0.145 kg/tDS amylase was added, and liquefied at 95° C. for 120 mins. After the reaction was completed, the DE and the viscosity of the sample were measured and a comparative test with Liquozyme Supra (available from Novozymes) was also conducted at the same time.

TABLE 9

Comparison of applications of amylases in corn alcohol liquefaction

| Ratio of feed to water | DE (%) | Viscosity (mPas) |
|---|---|---|
| Amylase - 1:2 | 12.36 | 1529 |
| Amylase - 1:2.3 | 12.95 | 1007 |
| Amylase - 1:2.5 | 13.24 | 498 |
| Amylase - 1:2.7 | 13.64 | 381 |
| Liquozyme Supra - 1:2 | 12.19 | 1702 |
| Liquozyme Supra - 1:2.3 | 12.78 | 1114 |
| Liquozyme Supra - 1:2.5 | 12.88 | 506 |
| Liquozyme Supra - 1:2.7 | 13.32 | 352 |

As shown in Table 9, the α-amylase variant of the present invention could achieve the same application effect as Liquzoyme Supra, indicating that it could be applied to the corn alcohol industry.

In summary, according to the experimental results in the present invention, the series of L-type amylase variants have better heat resistance and pH tolerance, and can be applied to the liquefaction of high-strength starch slurry, and thus can be applied to the starch sugar industry and the alcohol industry.

Although the invention has been herein shown and described in what is perceived to be the most practical and preferred embodiments, it is to be understood that the invention is not intended to be limited to the specific embodiments set forth above. Accordingly, it is recognized that modifications may be made by one skilled in the art of the invention without departing from the spirit or intent of the invention and therefore, the invention is to be taken as including all reasonable equivalents to the subject matter of the appended claims. Any reference to claim elements in the singular, for example, using the article "a," "an," "the," or "said," is not to be construed as limiting the element to the singular.

The invention claimed is:

1. An α-amylase variant, comprising at least 95% identity to parental α-amylase of SEQ ID NO: 2, wherein the α-amylase variant comprises amino acid residues DGL at N-terminus in place of N-terminal amino acid residue V of the parental α-amylase, and wherein the α-amylase variant still retains the ability of the parental α-amylase to hydrolyze α-1,4 glycosidic bonds.

2. The α-amylase variant according to claim 1, wherein the amino acid sequence of the α-amylase variant is set forth in SEQ ID NO: 4.

3. The α-amylase variant according to claim 2, wherein the nucleotide sequence encoding the α-amylase variant is set forth in SEQ ID NO: 3.

4. A gene encoding the α-amylase variant according to claim 1.

5. The gene according to claim 4, wherein the amino acid sequence of the 60 -amylase variant is set forth in SEQ ID NO: 4.

6. The gene according to claim 5, wherein the gene is set forth in SEQ ID NO: 3.

7. A method for producing the α-amylase variant according to claim 1, comprising: culturing a recombinant cell comprising a gene sequence encoding the α-amylase variant under conditions suitable for the expression of the α-amylase variant, and obtaining the α-amylase variant from the recombinant cell or its culture supernatant.

8. The method according to claim 7, wherein the amino acid sequence of the α-amylase variant is set forth in SEQ ID NO: 4.

9. The method according to claim 8, wherein the nucleotide sequence encoding the α-amylase variant is set forth in SEQ ID NO: 3.

* * * * *

SEQUENCE LISTING

<160> NUMBER OF SEQ ID NOS: 19

<210> SEQ ID NO 1
<211> LENGTH: 1446
<212> TYPE: DNA
<213> ORGANISM: Bacillus licheniformis
<220> FEATURE:
<221> NAME/KEY: CDS
<222> LOCATION: (1)..(1446)

<400> SEQUENCE: 1

| gta | aat | ggc | acg | ctc | atg | cag | tat | ttt | gaa | tgg | tat | act | ccg | aac | gac | 48 |
|---|---|---|---|---|---|---|---|---|---|---|---|---|---|---|---|---|
| Val | Asn | Gly | Thr | Leu | Met | Gln | Tyr | Phe | Glu | Trp | Tyr | Thr | Pro | Asn | Asp | |
| 1 | | | | 5 | | | | | 10 | | | | | 15 | | |

| ggc | cag | cat | tgg | aaa | cgg | ttg | cag | aat | gat | gcg | gaa | cat | ttg | tcg | gat | 96 |
|---|---|---|---|---|---|---|---|---|---|---|---|---|---|---|---|---|
| Gly | Gln | His | Trp | Lys | Arg | Leu | Gln | Asn | Asp | Ala | Glu | His | Leu | Ser | Asp | |
| | | | 20 | | | | | 25 | | | | | 30 | | | |

| atc | ggt | att | act | gcc | gtc | tgg | att | ccc | ccg | gca | tat | aag | gga | acg | agc | 144 |
|---|---|---|---|---|---|---|---|---|---|---|---|---|---|---|---|---|
| Ile | Gly | Ile | Thr | Ala | Val | Trp | Ile | Pro | Pro | Ala | Tyr | Lys | Gly | Thr | Ser | |
| | | 35 | | | | | 40 | | | | | 45 | | | | |

| caa | gcg | gat | gtg | ggc | tac | ggt | gct | tac | gac | ctt | tat | gat | tta | ggg | gag | 192 |
|---|---|---|---|---|---|---|---|---|---|---|---|---|---|---|---|---|
| Gln | Ala | Asp | Val | Gly | Tyr | Gly | Ala | Tyr | Asp | Leu | Tyr | Asp | Leu | Gly | Glu | |
| 50 | | | | | 55 | | | | | 60 | | | | | | |

| ttt | cat | caa | aaa | ggg | acg | gtt | cgg | aca | aag | tac | ggc | aca | aaa | gga | gag | 240 |
|---|---|---|---|---|---|---|---|---|---|---|---|---|---|---|---|---|
| Phe | His | Gln | Lys | Gly | Thr | Val | Arg | Thr | Lys | Tyr | Gly | Thr | Lys | Gly | Glu | |
| 65 | | | | 70 | | | | | 75 | | | | | 80 | | |

| ctg | caa | tct | gcg | atc | aaa | agt | ctt | cat | tcc | cgc | gac | att | aac | gtt | tac | 288 |
|---|---|---|---|---|---|---|---|---|---|---|---|---|---|---|---|---|
| Leu | Gln | Ser | Ala | Ile | Lys | Ser | Leu | His | Ser | Arg | Asp | Ile | Asn | Val | Tyr | |
| | | | | 85 | | | | | 90 | | | | | 95 | | |

| ggg | gat | gtg | gtc | atc | aac | cac | aaa | ggc | ggc | gct | gat | gcg | acc | gaa | gat | 336 |
|---|---|---|---|---|---|---|---|---|---|---|---|---|---|---|---|---|
| Gly | Asp | Val | Val | Ile | Asn | His | Lys | Gly | Gly | Ala | Asp | Ala | Thr | Glu | Asp | |
| | | | 100 | | | | | 105 | | | | | 110 | | | |

| gta | acc | gcg | gtt | gaa | gtc | gat | ccc | gct | gac | cgc | aac | cgc | gta | att | tca | 384 |
|---|---|---|---|---|---|---|---|---|---|---|---|---|---|---|---|---|
| Val | Thr | Ala | Val | Glu | Val | Asp | Pro | Ala | Asp | Arg | Asn | Arg | Val | Ile | Ser | |
| | | 115 | | | | | 120 | | | | | 125 | | | | |

| gga | gaa | cac | cta | att | aaa | gcc | tgg | aca | cat | ttt | cat | ttt | ccg | ggg | cgc | 432 |
|---|---|---|---|---|---|---|---|---|---|---|---|---|---|---|---|---|
| Gly | Glu | His | Leu | Ile | Lys | Ala | Trp | Thr | His | Phe | His | Phe | Pro | Gly | Arg | |
| 130 | | | | | 135 | | | | | 140 | | | | | | |

| ggc | agc | aca | tac | agc | gat | ttt | aaa | tgg | cat | tgg | tac | cat | ttt | gac | gga | 480 |
|---|---|---|---|---|---|---|---|---|---|---|---|---|---|---|---|---|
| Gly | Ser | Thr | Tyr | Ser | Asp | Phe | Lys | Trp | His | Trp | Tyr | His | Phe | Asp | Gly | |
| 145 | | | | | 150 | | | | | 155 | | | | | 160 | |

| acc | gat | tgg | gac | gag | tcc | cga | aag | ctg | aac | cgc | atc | tat | aag | ttt | caa | 528 |
|---|---|---|---|---|---|---|---|---|---|---|---|---|---|---|---|---|
| Thr | Asp | Trp | Asp | Glu | Ser | Arg | Lys | Leu | Asn | Arg | Ile | Tyr | Lys | Phe | Gln | |
| | | | | 165 | | | | | 170 | | | | | 175 | | |

| gga | aag | gct | tgg | gat | tgg | gaa | gtt | tcc | aat | gaa | aac | ggc | aac | tat | gat | 576 |
|---|---|---|---|---|---|---|---|---|---|---|---|---|---|---|---|---|
| Gly | Lys | Ala | Trp | Asp | Trp | Glu | Val | Ser | Asn | Glu | Asn | Gly | Asn | Tyr | Asp | |
| | | | 180 | | | | | 185 | | | | | 190 | | | |

| tat | ttg | atg | tat | gcc | gac | atc | gat | tat | gac | cat | cct | gat | gtc | gca | gca | 624 |
|---|---|---|---|---|---|---|---|---|---|---|---|---|---|---|---|---|
| Tyr | Leu | Met | Tyr | Ala | Asp | Ile | Asp | Tyr | Asp | His | Pro | Asp | Val | Ala | Ala | |
| | | 195 | | | | | 200 | | | | | 205 | | | | |

| gaa | att | aag | aga | tgg | ggc | act | tgg | tat | gcc | aat | gaa | ctg | caa | ttg | gac | 672 |
|---|---|---|---|---|---|---|---|---|---|---|---|---|---|---|---|---|
| Glu | Ile | Lys | Arg | Trp | Gly | Thr | Trp | Tyr | Ala | Asn | Glu | Leu | Gln | Leu | Asp | |
| | 210 | | | | | 215 | | | | | 220 | | | | | |

| ggt | ttc | cgt | ctt | gat | gct | gtc | aaa | cac | att | aaa | ttt | tct | ttt | ttg | cgg | 720 |
|---|---|---|---|---|---|---|---|---|---|---|---|---|---|---|---|---|
| Gly | Phe | Arg | Leu | Asp | Ala | Val | Lys | His | Ile | Lys | Phe | Ser | Phe | Leu | Arg | |
| 225 | | | | | 230 | | | | | 235 | | | | | 240 | |

| gat | tgg | gtt | aat | cat | gtc | agg | gaa | aaa | acg | ggg | aag | gaa | atg | ttt | acg | 768 |
|---|---|---|---|---|---|---|---|---|---|---|---|---|---|---|---|---|
| Asp | Trp | Val | Asn | His | Val | Arg | Glu | Lys | Thr | Gly | Lys | Glu | Met | Phe | Thr | |
| | | | | 245 | | | | | 250 | | | | | 255 | | |

| gta | gct | gaa | tat | tgg | cag | aat | gac | ttg | ggc | gcg | ctg | gaa | aac | tat | ttg | 816 |
|---|---|---|---|---|---|---|---|---|---|---|---|---|---|---|---|---|
| Val | Ala | Glu | Tyr | Trp | Gln | Asn | Asp | Leu | Gly | Ala | Leu | Glu | Asn | Tyr | Leu | |

```
aac aaa aca aat ttt aat cat tca gtg ttt gac gtg ccg ctt cat tat         864
Asn Lys Thr Asn Phe Asn His Ser Val Phe Asp Val Pro Leu His Tyr
        275                 280                 285 cag ttc cat gct gca tcg aca cag gga ggc ggc tat gat atg agg aaa         912
Gln Phe His Ala Ala Ser Thr Gln Gly Gly Gly Tyr Asp Met Arg Lys
        290                 295                 300 ttg ctg aac ggt acg gtc gtt tcc aag cat ccg ttg aaa tcg gtt aca         960
Leu Leu Asn Gly Thr Val Val Ser Lys His Pro Leu Lys Ser Val Thr
305                 310                 315                 320 ttt gtc gat aac cat gat aca cag ccg ggg caa tcg ctt gag tcg act        1008
Phe Val Asp Asn His Asp Thr Gln Pro Gly Gln Ser Leu Glu Ser Thr
                325                 330                 335 gtc caa aca tgg ttt aag ccg ctt gct tac gct ttt att ctc aca agg        1056
Val Gln Thr Trp Phe Lys Pro Leu Ala Tyr Ala Phe Ile Leu Thr Arg
        340                 345                 350 gaa tct gga tac cct cag gtt ttc tac ggg gat atg tac ggg acg aaa        1104
Glu Ser Gly Tyr Pro Gln Val Phe Tyr Gly Asp Met Tyr Gly Thr Lys
        355                 360                 365 gga gac tcc cag cgc gaa att cct gcc ttg aaa cac aaa att gaa ccg        1152
Gly Asp Ser Gln Arg Glu Ile Pro Ala Leu Lys His Lys Ile Glu Pro
370                 375                 380 atc tta aaa gcg aga aaa cag tat gcg tac gga gca cag cat gat tat        1200
Ile Leu Lys Ala Arg Lys Gln Tyr Ala Tyr Gly Ala Gln His Asp Tyr
385                 390                 395                 400 ttc gac cac cat gac att gtc ggc tgg aca agg gaa ggc gac agc tcg        1248
Phe Asp His His Asp Ile Val Gly Trp Thr Arg Glu Gly Asp Ser Ser
                405                 410                 415 gtt gca aat tca ggt ttg gcg gca tta ata aca gac gga ccc ggt ggg        1296
Val Ala Asn Ser Gly Leu Ala Ala Leu Ile Thr Asp Gly Pro Gly Gly
        420                 425                 430 gca aag cga atg tat gtc ggc cgg caa aac gcc ggt gag aca tgg cat        1344
Ala Lys Arg Met Tyr Val Gly Arg Gln Asn Ala Gly Glu Thr Trp His
        435                 440                 445 gac att acc gga aac cgt tcg gag ccg gtt gtc atc aat tcg gaa ggc        1392
Asp Ile Thr Gly Asn Arg Ser Glu Pro Val Val Ile Asn Ser Glu Gly
450                 455                 460 tgg gga gag ttt cac gta aac ggc ggg tcg gtt tca att tat gtt caa        1440
Trp Gly Glu Phe His Val Asn Gly Gly Ser Val Ser Ile Tyr Val Gln
465                 470                 475                 480 aga taa                                                                1446
Arg

<210> SEQ ID NO 2
<211> LENGTH: 481
<212> TYPE: PRT
<213> ORGANISM: Bacillus licheniformis

<400> SEQUENCE: 2

Val Asn Gly Thr Leu Met Gln Tyr Phe Glu Trp Tyr Thr Pro Asn Asp
1               5                   10                  15

Gly Gln His Trp Lys Arg Leu Gln Asn Asp Ala Glu His Leu Ser Asp
                20                  25                  30

Ile Gly Ile Thr Ala Val Trp Ile Pro Pro Ala Tyr Lys Gly Thr Ser
            35                  40                  45

Gln Ala Asp Val Gly Tyr Gly Ala Tyr Asp Leu Tyr Asp Leu Gly Glu
        50                  55                  60

Phe His Gln Lys Gly Thr Val Arg Thr Lys Tyr Gly Thr Lys Gly Glu
65                  70                  75                  80
```

-continued

```
Leu Gln Ser Ala Ile Lys Ser Leu His Ser Arg Asp Ile Asn Val Tyr
                85                  90                  95
Gly Asp Val Val Ile Asn His Lys Gly Ala Asp Ala Thr Glu Asp
            100                 105                 110
Val Thr Ala Val Glu Val Asp Pro Ala Asp Arg Asn Arg Val Ile Ser
            115                 120                 125
Gly Glu His Leu Ile Lys Ala Trp Thr His Phe His Phe Pro Gly Arg
        130                 135                 140
Gly Ser Thr Tyr Ser Asp Phe Lys Trp His Trp Tyr His Phe Asp Gly
145                 150                 155                 160
Thr Asp Trp Asp Glu Ser Arg Lys Leu Asn Arg Ile Tyr Lys Phe Gln
                165                 170                 175
Gly Lys Ala Trp Asp Trp Glu Val Ser Asn Glu Asn Gly Asn Tyr Asp
            180                 185                 190
Tyr Leu Met Tyr Ala Asp Ile Asp Tyr Asp His Pro Asp Val Ala Ala
        195                 200                 205
Glu Ile Lys Arg Trp Gly Thr Trp Tyr Ala Asn Glu Leu Gln Leu Asp
        210                 215                 220
Gly Phe Arg Leu Asp Ala Val Lys His Ile Lys Phe Ser Phe Leu Arg
225                 230                 235                 240
Asp Trp Val Asn His Val Arg Glu Lys Thr Gly Lys Glu Met Phe Thr
                245                 250                 255
Val Ala Glu Tyr Trp Gln Asn Asp Leu Gly Ala Leu Glu Asn Tyr Leu
            260                 265                 270
Asn Lys Thr Asn Phe Asn His Ser Val Phe Asp Val Pro Leu His Tyr
        275                 280                 285
Gln Phe His Ala Ala Ser Thr Gln Gly Gly Gly Tyr Asp Met Arg Lys
        290                 295                 300
Leu Leu Asn Gly Thr Val Val Ser Lys His Pro Leu Lys Ser Val Thr
305                 310                 315                 320
Phe Val Asp Asn His Asp Thr Gln Pro Gly Gln Ser Leu Glu Ser Thr
                325                 330                 335
Val Gln Thr Trp Phe Lys Pro Leu Ala Tyr Ala Phe Ile Leu Thr Arg
            340                 345                 350
Glu Ser Gly Tyr Pro Gln Val Phe Tyr Gly Asp Met Tyr Gly Thr Lys
        355                 360                 365
Gly Asp Ser Gln Arg Glu Ile Pro Ala Leu Lys His Lys Ile Glu Pro
        370                 375                 380
Ile Leu Lys Ala Arg Lys Gln Tyr Ala Tyr Gly Ala Gln His Asp Tyr
385                 390                 395                 400
Phe Asp His His Asp Ile Val Gly Trp Thr Arg Glu Gly Asp Ser Ser
                405                 410                 415
Val Ala Asn Ser Gly Leu Ala Ala Leu Ile Thr Asp Gly Pro Gly Gly
            420                 425                 430
Ala Lys Arg Met Tyr Val Gly Arg Gln Asn Ala Gly Glu Thr Trp His
        435                 440                 445
Asp Ile Thr Gly Asn Arg Ser Glu Pro Val Val Ile Asn Ser Glu Gly
        450                 455                 460
Trp Gly Glu Phe His Val Asn Gly Gly Ser Val Ser Ile Tyr Val Gln
465                 470                 475                 480
Arg
```

```
<210> SEQ ID NO 3
<211> LENGTH: 1452
<212> TYPE: DNA
<213> ORGANISM: Artificial Sequence
<220> FEATURE:
<223> OTHER INFORMATION: alpha-amylase variant
<220> FEATURE:
<221> NAME/KEY: CDS
<222> LOCATION: (1)..(1452)

<400> SEQUENCE: 3 gat ggg ctg aat ggc acg ctc atg cag tat ttt gaa tgg tat act ccg      48
Asp Gly Leu Asn Gly Thr Leu Met Gln Tyr Phe Glu Trp Tyr Thr Pro
 1               5                  10                  15 aac gac ggc cag cat tgg aaa cgg ttg cag aat gat gcg gaa cat ttg      96
Asn Asp Gly Gln His Trp Lys Arg Leu Gln Asn Asp Ala Glu His Leu
            20                  25                  30 tcg gat atc ggt att act gcc gtc tgg att ccc ccg gca tat aag gga     144
Ser Asp Ile Gly Ile Thr Ala Val Trp Ile Pro Pro Ala Tyr Lys Gly
        35                  40                  45 acg agc caa gcg gat gtg ggc tac ggt gct tac gac ctt tat gat tta     192
Thr Ser Gln Ala Asp Val Gly Tyr Gly Ala Tyr Asp Leu Tyr Asp Leu
    50                  55                  60 ggg gag ttt cat caa aaa ggg acg gtt cgg aca aag tac ggc aca aaa     240
Gly Glu Phe His Gln Lys Gly Thr Val Arg Thr Lys Tyr Gly Thr Lys
65                  70                  75                  80 gga gag ctg caa tct gcg atc aaa agt ctt cat tcc cgc gac att aac     288
Gly Glu Leu Gln Ser Ala Ile Lys Ser Leu His Ser Arg Asp Ile Asn
                85                  90                  95 gtt tac ggg gat gtg gtc atc aac cac aaa ggc ggc gct gat gcg acc     336
Val Tyr Gly Asp Val Val Ile Asn His Lys Gly Gly Ala Asp Ala Thr
            100                 105                 110 gaa gat gta acc gcg gtt gaa gtc gat ccc gct gac cgc aac cgc gta     384
Glu Asp Val Thr Ala Val Glu Val Asp Pro Ala Asp Arg Asn Arg Val
        115                 120                 125 att tca gga gaa cac cta att aaa gcc tgg aca cat ttt cat ttt ccg     432
Ile Ser Gly Glu His Leu Ile Lys Ala Trp Thr His Phe His Phe Pro
    130                 135                 140 ggg cgc ggc agc aca tac agc gat ttt aaa tgg cat tgg tac cat ttt     480
Gly Arg Gly Ser Thr Tyr Ser Asp Phe Lys Trp His Trp Tyr His Phe
145                 150                 155                 160 gac gga acc gat tgg gac gag tcc cga aag ctg aac cgc atc tat aag     528
Asp Gly Thr Asp Trp Asp Glu Ser Arg Lys Leu Asn Arg Ile Tyr Lys
                165                 170                 175 ttt caa gga aag gct tgg gat tgg gaa gtt tcc aat gaa aac ggc aac     576
Phe Gln Gly Lys Ala Trp Asp Trp Glu Val Ser Asn Glu Asn Gly Asn
            180                 185                 190 tat gat tat ttg atg tat gcc gac atc gat tat gac cat cct gat gtc     624
Tyr Asp Tyr Leu Met Tyr Ala Asp Ile Asp Tyr Asp His Pro Asp Val
        195                 200                 205 gca gca gaa att aag aga tgg ggc act tgg tat gcc aat gaa ctg caa     672
Ala Ala Glu Ile Lys Arg Trp Gly Thr Trp Tyr Ala Asn Glu Leu Gln
    210                 215                 220 ttg gac ggt ttc cgt ctt gat gct gtc aaa cac att aaa ttt tct ttt     720
Leu Asp Gly Phe Arg Leu Asp Ala Val Lys His Ile Lys Phe Ser Phe
225                 230                 235                 240 ttg cgg gat tgg gtt aat cat gtc agg gaa aaa acg ggg aag gaa atg     768
Leu Arg Asp Trp Val Asn His Val Arg Glu Lys Thr Gly Lys Glu Met
                245                 250                 255 ttt acg gta gct gaa tat tgg cag aat gac ttg ggc gcg ctg gaa aac     816
Phe Thr Val Ala Glu Tyr Trp Gln Asn Asp Leu Gly Ala Leu Glu Asn
            260                 265                 270
```

-continued

| | | |
|---|---|---|
| tat ttg aac aaa aca aat ttt aat cat tca gtg ttt gac gtg ccg ctt<br>Tyr Leu Asn Lys Thr Asn Phe Asn His Ser Val Phe Asp Val Pro Leu<br>275 280 285 | | 864 |
| cat tat cag ttc cat gct gca tcg aca cag gga ggc ggc tat gat atg<br>His Tyr Gln Phe His Ala Ala Ser Thr Gln Gly Gly Gly Tyr Asp Met<br>290 295 300 | | 912 |
| agg aaa ttg ctg aac ggt acg gtc gtt tcc aag cat ccg ttg aaa tcg<br>Arg Lys Leu Leu Asn Gly Thr Val Val Ser Lys His Pro Leu Lys Ser<br>305 310 315 320 | | 960 |
| gtt aca ttt gtc gat aac cat gat aca cag ccg ggg caa tcg ctt gag<br>Val Thr Phe Val Asp Asn His Asp Thr Gln Pro Gly Gln Ser Leu Glu<br>325 330 335 | | 1008 |
| tcg act gtc caa aca tgg ttt aag ccg ctt gct tac gct ttt att ctc<br>Ser Thr Val Gln Thr Trp Phe Lys Pro Leu Ala Tyr Ala Phe Ile Leu<br>340 345 350 | | 1056 |
| aca agg gaa tct gga tac cct cag gtt ttc tac ggg gat atg tac ggg<br>Thr Arg Glu Ser Gly Tyr Pro Gln Val Phe Tyr Gly Asp Met Tyr Gly<br>355 360 365 | | 1104 |
| acg aaa gga gac tcc cag cgc gaa att cct gcc ttg aaa cac aaa att<br>Thr Lys Gly Asp Ser Gln Arg Glu Ile Pro Ala Leu Lys His Lys Ile<br>370 375 380 | | 1152 |
| gaa ccg atc tta aaa gcg aga aaa cag tat gcg tac gga gca cag cat<br>Glu Pro Ile Leu Lys Ala Arg Lys Gln Tyr Ala Tyr Gly Ala Gln His<br>385 390 395 400 | | 1200 |
| gat tat ttc gac cac cat gac att gtc ggc tgg aca agg gaa ggc gac<br>Asp Tyr Phe Asp His His Asp Ile Val Gly Trp Thr Arg Glu Gly Asp<br>405 410 415 | | 1248 |
| agc tcg gtt gca aat tca ggt ttg gcg gca tta ata aca gac gga ccc<br>Ser Ser Val Ala Asn Ser Gly Leu Ala Ala Leu Ile Thr Asp Gly Pro<br>420 425 430 | | 1296 |
| ggt ggg gca aag cga atg tat gtc ggc cgg caa aac gcc ggt gag aca<br>Gly Gly Ala Lys Arg Met Tyr Val Gly Arg Gln Asn Ala Gly Glu Thr<br>435 440 445 | | 1344 |
| tgg cat gac att acc gga aac cgt tcg gag ccg gtt gtc atc aat tcg<br>Trp His Asp Ile Thr Gly Asn Arg Ser Glu Pro Val Val Ile Asn Ser<br>450 455 460 | | 1392 |
| gaa ggc tgg gga gag ttt cac gta aac ggc ggg tcg gtt tca att tat<br>Glu Gly Trp Gly Glu Phe His Val Asn Gly Gly Ser Val Ser Ile Tyr<br>465 470 475 480 | | 1440 |
| gtt caa aga taa<br>Val Gln Arg | | 1452 |

<210> SEQ ID NO 4
<211> LENGTH: 483
<212> TYPE: PRT
<213> ORGANISM: Artificial Sequence
<220> FEATURE:
<223> OTHER INFORMATION: Synthetic Construct

<400> SEQUENCE: 4

Asp Gly Leu Asn Gly Thr Leu Met Gln Tyr Phe Glu Trp Tyr Thr Pro
1               5                   10                  15

Asn Asp Gly Gln His Trp Lys Arg Leu Gln Asn Asp Ala Glu His Leu
            20                  25                  30

Ser Asp Ile Gly Ile Thr Ala Val Trp Ile Pro Pro Ala Tyr Lys Gly
        35                  40                  45

Thr Ser Gln Ala Asp Val Gly Tyr Gly Ala Tyr Asp Leu Tyr Asp Leu
    50                  55                  60

Gly Glu Phe His Gln Lys Gly Thr Val Arg Thr Lys Tyr Gly Thr Lys

```
            65                  70                  75                  80
        Gly Glu Leu Gln Ser Ala Ile Lys Ser Leu His Ser Arg Asp Ile Asn
                            85                  90                  95
        Val Tyr Gly Asp Val Val Ile Asn His Lys Gly Gly Ala Asp Ala Thr
                        100                 105                 110
        Glu Asp Val Thr Ala Val Glu Val Asp Pro Ala Asp Arg Asn Arg Val
                    115                 120                 125
        Ile Ser Gly Glu His Leu Ile Lys Ala Trp Thr His Phe His Phe Pro
                130                 135                 140
        Gly Arg Gly Ser Thr Tyr Ser Asp Phe Lys Trp His Trp Tyr His Phe
        145                 150                 155                 160
        Asp Gly Thr Asp Trp Asp Glu Ser Arg Lys Leu Asn Arg Ile Tyr Lys
                        165                 170                 175
        Phe Gln Gly Lys Ala Trp Asp Trp Glu Val Ser Asn Glu Asn Gly Asn
                    180                 185                 190
        Tyr Asp Tyr Leu Met Tyr Ala Asp Ile Asp Tyr Asp His Pro Asp Val
                195                 200                 205
        Ala Ala Glu Ile Lys Arg Trp Gly Thr Trp Tyr Ala Asn Glu Leu Gln
            210                 215                 220
        Leu Asp Gly Phe Arg Leu Asp Ala Val Lys His Ile Lys Phe Ser Phe
        225                 230                 235                 240
        Leu Arg Asp Trp Val Asn His Val Arg Glu Lys Thr Gly Lys Glu Met
                        245                 250                 255
        Phe Thr Val Ala Glu Tyr Trp Gln Asn Asp Leu Gly Ala Leu Glu Asn
                    260                 265                 270
        Tyr Leu Asn Lys Thr Asn Phe Asn His Ser Val Phe Asp Val Pro Leu
                275                 280                 285
        His Tyr Gln Phe His Ala Ala Ser Thr Gln Gly Gly Tyr Asp Met
            290                 295                 300
        Arg Lys Leu Leu Asn Gly Thr Val Val Ser Lys His Pro Leu Lys Ser
        305                 310                 315                 320
        Val Thr Phe Val Asp Asn His Asp Thr Gln Pro Gly Gln Ser Leu Glu
                        325                 330                 335
        Ser Thr Val Gln Thr Trp Phe Lys Pro Leu Ala Tyr Ala Phe Ile Leu
                    340                 345                 350
        Thr Arg Glu Ser Gly Tyr Pro Gln Val Phe Tyr Gly Asp Met Tyr Gly
                355                 360                 365
        Thr Lys Gly Asp Ser Gln Arg Glu Ile Pro Ala Leu Lys His Lys Ile
            370                 375                 380
        Glu Pro Ile Leu Lys Ala Arg Lys Gln Tyr Ala Tyr Gly Ala Gln His
        385                 390                 395                 400
        Asp Tyr Phe Asp His His Asp Ile Val Gly Trp Thr Arg Glu Gly Asp
                        405                 410                 415
        Ser Ser Val Ala Asn Ser Gly Leu Ala Ala Leu Ile Thr Asp Gly Pro
                    420                 425                 430
        Gly Gly Ala Lys Arg Met Tyr Val Gly Arg Gln Asn Ala Gly Glu Thr
                435                 440                 445
        Trp His Asp Ile Thr Gly Asn Arg Ser Glu Pro Val Val Ile Asn Ser
            450                 455                 460
        Glu Gly Trp Gly Glu Phe His Val Asn Gly Gly Ser Val Ser Ile Tyr
        465                 470                 475                 480
        Val Gln Arg
```

<210> SEQ ID NO 5
<211> LENGTH: 873
<212> TYPE: DNA
<213> ORGANISM: Artificial Sequence
<220> FEATURE:
<223> OTHER INFORMATION: synthetic promoter sequence

<400> SEQUENCE: 5

```
ggtaccagct attgtaacat aatcggtacg ggggtgaaaa agctaacgga aaagggagcg      60
gaaaagaatg atgtaagcgt gaaaaatttt ttatcttatc acttgaaatt ggaagggaga     120
ttctttatta taagaaaacg gatgctgaag gaaggaaacg aagtcggcaa ccattcctgg     180
gaccatccgt tattgacaag gctgtcaaat gaaaaagcgt atcaggagat taacgacacg     240
caagaaatga tcgaaaaaat cagcggacac ctgcctgtac acttgcgtcc tccatacggc     300
gggatcaatg attccgtccg ctcgctttcc aatctgaagg tttcattgtg ggatgttgat     360
ccggaagatt ggaagtacaa aaataagcaa aagattgtca atcatgtcat gagccatgcg     420
ggagacggaa aaatcgtctt aatgcacgat atttatgcaa cgtccgcaga tgctgctgaa     480
gagattatta aaaagctgaa agcaaaaggc tatcaattgg taactgtatc tcagcttgaa     540
gaagtgaaga agcagagagg ctattgaata atgagtagaa agcgccata tcggcgcttt      600 tcttttggaa gaaatatag ggaaaatggt atttgttaaa aattctgaat atttatacaa      660
tatcatatgt ttcacaggga ggagaatcgg ccttaagggc ctgcaatcga ttgtttgaga     720
aaagaagaag accataaaaa taccttgtct gtcatcagac agggtatttt ttatgctgtc     780
cagactgtcc gctgtgtaaa aaaaggaat aaaggggggt tgacattatt ttactgatat      840
gtataatata atttgtataa gaaaatggag ctc                                 873
```

<210> SEQ ID NO 6
<211> LENGTH: 98
<212> TYPE: DNA
<213> ORGANISM: Artificial Sequence
<220> FEATURE:
<223> OTHER INFORMATION: synthetic termination sequence

<400> SEQUENCE: 6

```
tcaataataa taacgctgtg tgctttaagc acacagcgtt ttttagtgtg tatgaatcga      60
gatcctgagc gccggtcgct accattacca gttggtct                             98
```

<210> SEQ ID NO 7
<211> LENGTH: 96
<212> TYPE: DNA
<213> ORGANISM: Artificial Sequence
<220> FEATURE:
<223> OTHER INFORMATION: natural signal sequence

<400> SEQUENCE: 7

```
atgattcaaa aacgaaagcg gacagtttcg ttcagacttg tgcttatgtg cacgctgtta      60
tttgtcagtt tgccgattac aaaaacatca gccgca                               96
```

<210> SEQ ID NO 8
<211> LENGTH: 35
<212> TYPE: DNA
<213> ORGANISM: Artificial Sequence
<220> FEATURE:
<223> OTHER INFORMATION: forward primer for amplifying the upstream
      sequence of the Apr gene

<400> SEQUENCE: 8
ttattgagcg gcagcttcga cattgatcag acctt            35

<210> SEQ ID NO 9
<211> LENGTH: 34
<212> TYPE: DNA
<213> ORGANISM: Artificial Sequence
<220> FEATURE:
<223> OTHER INFORMATION: reverse primer for amplifying the upstream
      sequence of the Apr gene

<400> SEQUENCE: 9
ccttacggca ttcctctcaa cagcggatct tcag            34

<210> SEQ ID NO 10
<211> LENGTH: 35
<212> TYPE: DNA
<213> ORGANISM: Artificial Sequence
<220> FEATURE:
<223> OTHER INFORMATION: forward primer for amplifying the downstream
      sequence of the Apr gene

<400> SEQUENCE: 10
cctgaagatc cgctgttgag aggaatgccg taagg            35

<210> SEQ ID NO 11
<211> LENGTH: 38
<212> TYPE: DNA
<213> ORGANISM: Artificial Sequence
<220> FEATURE:
<223> OTHER INFORMATION: reverse primer for amplifying the downstream
      sequence of the Apr gene

<400> SEQUENCE: 11
atgatgagga aaagagtttt ttggcttggg atgctgac            38

<210> SEQ ID NO 12
<211> LENGTH: 37
<212> TYPE: DNA
<213> ORGANISM: Artificial Sequence
<220> FEATURE:
<223> OTHER INFORMATION: forward primer for amplifying the upstream
      sequence of the Blase gene

<400> SEQUENCE: 12
ttattgtgcg ctgttttttcc agttggtcaa attgtcg            37

<210> SEQ ID NO 13
<211> LENGTH: 36
<212> TYPE: DNA
<213> ORGANISM: Artificial Sequence
<220> FEATURE:
<223> OTHER INFORMATION: reverse primer for amplifying the upstream
      sequence of the Blase gene

<400> SEQUENCE: 13
cggacaaggg tcaccaacgg gacaactgtt accatc            36

<210> SEQ ID NO 14
<211> LENGTH: 35
<212> TYPE: DNA
<213> ORGANISM: Artificial Sequence
<220> FEATURE:
<223> OTHER INFORMATION: forward primer for amplifying the downstream
      sequence of the Blase gene

<400> SEQUENCE: 14
gatggtaaca gttgtcccgt tggtgaccct tgtcc            35

```
<210> SEQ ID NO 15
<211> LENGTH: 40
<212> TYPE: DNA
<213> ORGANISM: Artificial Sequence
<220> FEATURE:
<223> OTHER INFORMATION: reverse primer for amplifying the downstream
      sequence of the Blase gene

<400> SEQUENCE: 15
cggcgttggt tagtaaaaag agtgttaaac gaggtttgat                              40

<210> SEQ ID NO 16
<211> LENGTH: 24
<212> TYPE: DNA
<213> ORGANISM: Artificial Sequence
<220> FEATURE:
<223> OTHER INFORMATION: forward primer for identifying AprE

<400> SEQUENCE: 16
gccaggttga agcggtctat tcat                                              24

<210> SEQ ID NO 17
<211> LENGTH: 25
<212> TYPE: DNA
<213> ORGANISM: Artificial Sequence
<220> FEATURE:
<223> OTHER INFORMATION: reverse primer for identifying AprE

<400> SEQUENCE: 17
tacggccatc cgaccataat ggaac                                             25

<210> SEQ ID NO 18
<211> LENGTH: 20
<212> TYPE: DNA
<213> ORGANISM: Artificial Sequence
<220> FEATURE:
<223> OTHER INFORMATION: forward primer for identifying Blase

<400> SEQUENCE: 18
gaagagccgg tcacaattgc                                                   20

<210> SEQ ID NO 19
<211> LENGTH: 20
<212> TYPE: DNA
<213> ORGANISM: Artificial Sequence
<220> FEATURE:
<223> OTHER INFORMATION: reverse primer for identifying Blase

<400> SEQUENCE: 19
ggccgttaga tgtgacagcc                                                   20
```